United States Patent
Wolf

(10) Patent No.: US 9,222,917 B2
(45) Date of Patent: Dec. 29, 2015

(54) BROADBAND EDDY CURRENT PROBE

(75) Inventor: Matthew Barton Wolf, Boalsburg, PA (US)

(73) Assignee: General Electric Company, Schenectady, NY (US)

( * ) Notice: Subject to any disclaimer, the term of this patent is extended or adjusted under 35 U.S.C. 154(b) by 254 days.

(21) Appl. No.: 13/557,939

(22) Filed: Jul. 25, 2012

(65) Prior Publication Data

US 2014/0028302 A1   Jan. 30, 2014

(51) Int. Cl.
*G01N 27/82* (2006.01)
*G01N 27/90* (2006.01)

(52) U.S. Cl.
CPC ............ *G01N 27/9046* (2013.01); *G01N 27/90* (2013.01); *Y10T 29/49073* (2015.01)

(58) Field of Classification Search
CPC ...................................... G01N 27/90
USPC ................................. 324/241, 238
See application file for complete search history.

(56) References Cited

U.S. PATENT DOCUMENTS

| 2,104,646 | A | | 1/1938 | Greenslade |
| 3,437,918 | A | | 4/1969 | Arnelo |
| 4,107,605 | A | | 8/1978 | Hudgell |
| 4,620,152 | A | * | 10/1986 | Bains, Jr. ................. 324/225 |
| 5,017,869 | A | * | 5/1991 | Oliver ........................ 324/230 |
| 2004/0257072 | A1 | | 12/2004 | Samson |
| 2008/0278157 | A1 | | 11/2008 | Zimmerman |
| 2009/0255352 | A1 | | 10/2009 | Draper et al. |
| 2011/0068784 | A1 | | 3/2011 | Sun et al. |
| 2012/0006133 | A1 | | 1/2012 | Draper et al. |
| 2012/0006134 | A1 | | 1/2012 | Draper et al. |
| 2012/0153944 | A1 | | 6/2012 | Tada et al. |

FOREIGN PATENT DOCUMENTS

| CA | 1014226 A1 | 7/1977 |
| FR | 2314496 A1 | 1/1977 |
| FR | 2426257 A1 | 12/1979 |
| GB | 2019005 A | 10/1979 |

OTHER PUBLICATIONS

Search Report and Written Opinion from EP Application No. 13177228.7 dated Oct. 21, 2013.

* cited by examiner

*Primary Examiner* — Reena Aurora
(74) *Attorney, Agent, or Firm* — Barclay Damon, LLP

(57) ABSTRACT

An eddy current probe is constructed with four coils in a wheatstone bridge configuration.

16 Claims, 2 Drawing Sheets

BROADBAND EDDY CURRENT PROBE

BACKGROUND OF THE INVENTION

The subject matter disclosed herein relates to eddy current probes, in particular, to an eddy current probe useable over a wide range of frequencies.

Eddy current probes are a form of nondestructive testing devices that can be used to inspect test objects, such as tubes or pipes, to detect and analyze defects in the objects. Nondestructive testing allows an inspection technician to maneuver an eddy current probe through a test object in order to scan for defects.

In an eddy current probe, a magnetic field is used to induce an electrical current in the test object. The magnetic field is typically generated by one or two electrically conductive coils, or windings, in the probe. During operation of the probe an electrical current is sent through the coil, or coils, which generates a magnetic field that passes through the test object and induces an electrical current in the test object called an eddy current. The eddy current travels through a tube in a circular pathway along a circumference of the tube in a plane that is perpendicular to an axis of the tube.

If the induced eddy current passes through a flaw or defect in the test object, for example, erosion and pitting of the inside diameter of a tube, or if the inside diameter of the tube fluctuates as the probe travels through the tube, the induced eddy current is perturbed and the coils will detect this as a varying impedance. In response to detecting the varying impedance, the coils will generate electrical signals that represent physical characteristics of the defect. By analyzing these electrical signals, various characteristics of the defect (e.g., location, size) can be determined. Each of the coils will detect a different impedance variance because the coils are located at a different distance from the defect. The impedance difference detected by the coils can be converted into a two-dimensional impedance data display.

Typical eddy current probes have a limited testing frequency range because the two coils in the probe are balanced in a wheatstone bridge configuration against fixed resistors. The fixed resistors are typically located in a remote test instrument.

The discussion above is merely provided for general background information and is not intended to be used as an aid in determining the scope of the claimed subject matter.

BRIEF DESCRIPTION OF THE INVENTION

An eddy current probe is constructed with four coils in a wheatstone bridge configuration. An advantage that may be realized in the practice of some disclosed embodiments of the eddy current probe is that a wider range of frequencies can be employed during an inspection operation, thereby revealing higher resolution of defects in the objects undergoing inspection.

In one embodiment, an eddy current probe for detecting a defect in a test object is disclosed. The eddy current probe comprises a first coil and a second coil both electrically connected to a first voltage terminal, the first voltage terminal for receiving a drive voltage, a third coil and a fourth coil both electrically connected to a second voltage terminal, the second voltage terminal for receiving a ground, and wherein the first coil is electrically connected to the third coil at a first bridge terminal, the second coil is electrically connected to the fourth coil at a second bridge terminal, and wherein a voltage difference between the first and second bridge terminals indicates the defect in the test object when the four coils of the probe are inside the test object.

In another embodiment, a method of making an eddy current probe for inspecting a test object is disclosed. The method comprises winding a first, second, third, and fourth coil around a bobbin, electrically connecting the first coil and the second coil to a first voltage terminal, electrically connecting the third coil and the fourth coil to a second voltage terminal, electrically connecting the first coil and the third coil to a first bridge terminal, and electrically connecting the second coil and the fourth coil to a second bridge terminal.

In yet another embodiment, a system for analyzing a defect in a test object is disclosed. The system comprises an eddy current probe, the probe comprising a first coil and a second coil both electrically connected to a first voltage terminal, the first voltage terminal for receiving a drive voltage, a third coil and a fourth coil both electrically connected to a second voltage terminal, the second voltage terminal for connecting to a ground source, and wherein the first coil is electrically connected to the third coil at a first bridge terminal, wherein the second coil is electrically connected to the fourth coil at a second bridge terminal, and wherein a voltage difference between the first and second bridge terminals indicates a presence of the defect in the test object, and a test instrument comprising a drive voltage source electrically connected to the first terminal for providing the drive voltage, a ground source electrically connected to the second terminal for providing the ground, and a receiver amplifier electrically connected to the first and second bridge terminals for detecting a magnitude of the voltage difference.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
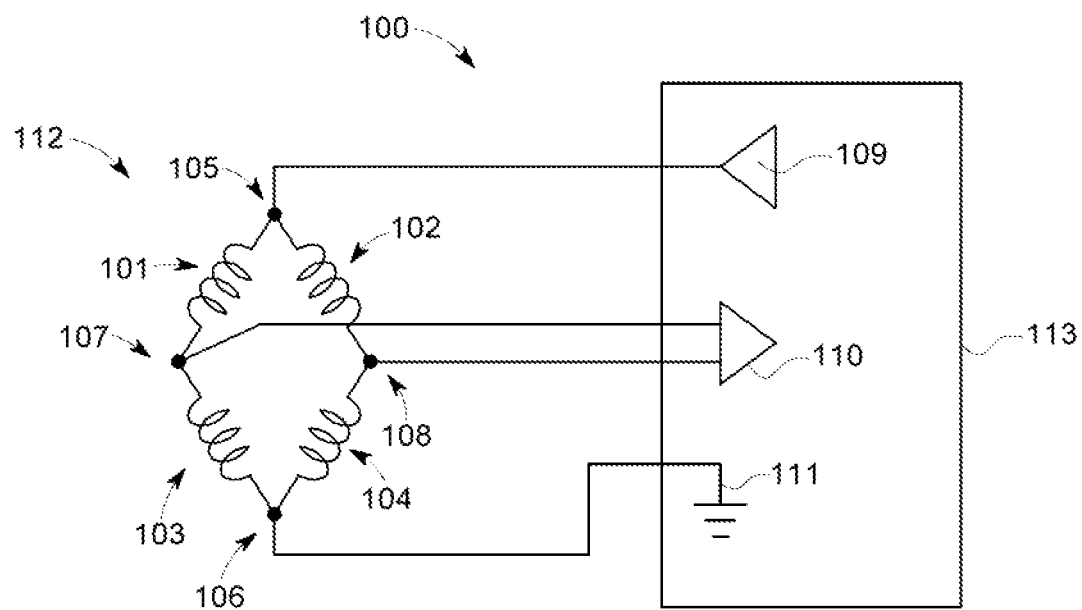
FIG. 1 is a schematic diagram of an exemplary eddy current testing system.

FIG. 1 illustrates a test system 100 comprising an eddy current probe circuit 112, in a wheatstone bridge configuration, connected to a test instrument 113. The eddy current probe circuit 112 comprises a first coil 101 and a second coil 102 electrically connected to a first voltage terminal 105 which, in turn, is electrically connected to a drive voltage source 109, for example a drive amplifier, in the test instrument 113. The eddy current probe circuit 112 further comprises a third coil 103 and a fourth coil 104 electrically connected to a second voltage terminal 106 which, in turn, is electrically connected to a ground source 111 in the test instrument 113. The drive voltage source 109 provides a drive voltage to the first, second, third and fourth coils 101, 102, 103, 104 through the first voltage terminal 105. The ground source 111 provides a ground to the first, second, third and fourth coils 101, 102, 103, 104 through the second voltage terminal 106. The ground source 111 is typically located in the test instrument 113 and is connected to second voltage terminal 106 via a coaxial cable. The ground source 111 need not be located in the test instrument 113, and the second voltage terminal 106 can be connected to a more convenient source of ground.

The first coil 101 and the third coil 103 are electrically connected together at a first bridge terminal 107, and the second coil 102 and the fourth coil 104 are electrically connected together at a second bridge terminal 108. Both the first and the second bridge terminals 107, 108 are electrically connected to a receiver amplifier 110 in the test instrument 113.

Figure 2:
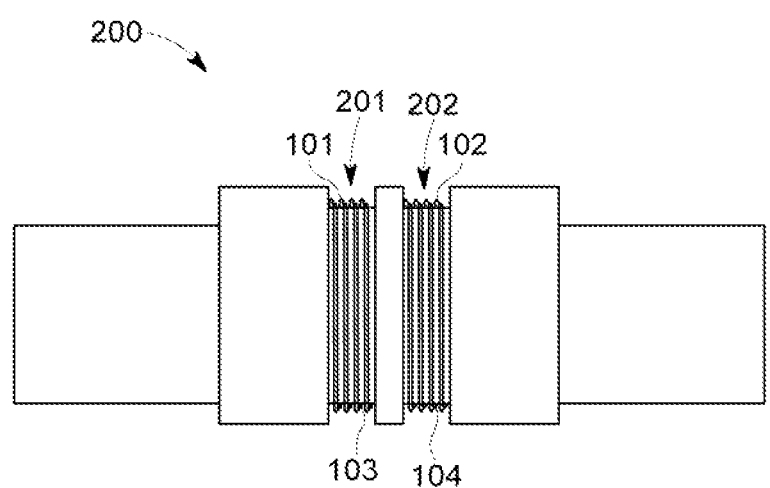
FIG. 2 is a diagram of a bobbin used for winding conductive wire to form four coils thereon.

FIG. 2 is a diagram of a bobbin 200 comprising a first winding section 201 and a second winding section 202. As an example method of forming the four coils 101-104 of the eddy current probe circuit 112 of FIG. 1, conductive wire is wound around first winding section 201 to form third coil 103. Additional conductive wire is wound around first winding section 201 over the winding of the third coil 103 therein to form first coil 101. To form the other two coils, conductive wire is then wound around second winding section 202 to form fourth coil 104. Additional conductive wire is wound around second winding section 202 over the winding of the fourth coil 104 therein to form second coil 102.

The first coil 101 and the third coil 103 in first winding section 201 are electrically connected together at first bridge terminal 107 which, in turn, is electrically connected to receiver amplifier 110 in the test instrument 113, as shown in FIG. 1, when the test system 100 is in operation. This equivalent to forming a center tap of a stacked coil in the first winding section 201 to separate the stacked coil into the two coils 101, 103, and electrically connecting the center tap, which is first bridge terminal 107, to receiver amplifier 110 in the test instrument 113.

The second coil 102 and the fourth coil 104 in second winding section 202 are electrically connected together at second bridge terminal 108 which, in turn, is electrically connected to receiver amplifier 110 in the test instrument 113, as shown in FIG. 1, when the test system 100 is in operation. This is equivalent to forming a center tap of a stacked coil in the second winding section 202 to separate it into two coils 102, 104, and electrically connecting the center tap, which is second bridge terminal 108, to receiver amplifier 110 in the test instrument 113.

Typical inductance values of the coils 101-104 are approximately 80 µH. For optimal performance of the probe, first coil 101 should have an inductance substantially equal to that of third coil 103, and second coil 102 should have an inductance substantially equal to that of fourth coil 104. The better balanced the coils 101-104 are with respect to their inductance values, the cleaner the defect detection signal from the probe will be. With respect to the magnetic field, when it's perturbed by a flaw during inspection, it will be detected differently by the top coils (first coil 101 and second coil 102) and the bottom coils (third coil 103 and fourth coil 104). The perturbation as detected by the first coil 101 is subtracted out from the perturbation as detected by the third coil 103 which provides a sharp resolution of the flaw. Because all the coils 101-104 of the probe circuit are located in the same probe housing, or probe package 300 (FIG. 3), any ambient temperature changes, or changes in the conditions of the testing environment during inspection, are less likely to disturb the balance of the four coils 101-104 because they are all closely packaged together. This is in contrast with other types of eddy current probe designs wherein some of the wheatstone bridge circuit elements are remotely located in the test instrument 113.

Figure 3:
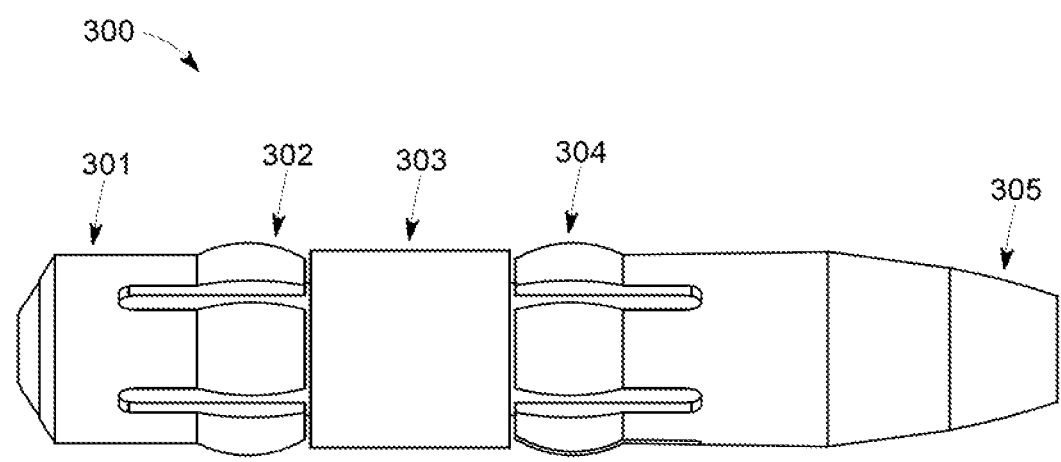
FIG. 3 is an example probe package for the probe configuration disclosed herein.

FIG. 3 is an eddy current probe package 300 that includes a probe head 301, a first centering foot 302 and a second centering foot 304. Located between the first centering foot 302 and the second centering foot 304 is the bobbin housing portion 303. Within the bobbin housing portion 303 there is disposed the eddy current probe circuit 112 comprising the first, second, third, and fourth coils 101, 102, 103, 104, first and second voltage terminals 105, 106, and the first and second bridge terminals 107, 108. Connecting portion 305 attaches to a shaft or cable, or multiple cables, that connects to the test instrument 113, which shaft, cable, or cables, includes electrical lines for electrically connecting first voltage terminal 105 to drive voltage source 109, second voltage terminal 106 to a ground source 111, and first and second bridge terminals 107, 108 to receiver amplifier 110, as previously described above. First centering foot 302 and second centering foot 304 should substantially match the inside diameter of a test object (e.g., tube or pipe) being inspected to maintain a uniform distance between the probe coils 101-104 and test object. A typical test object can include a carbon steel tube with aluminum fins.

In operation, probe package 300 is connected to test instrument 113 via a cable or cables, as described above. The drive voltage is applied to first voltage terminal 105 by the drive voltage source 109 in test instrument 113, and the ground is applied to the second voltage terminal 106 by the ground source 111 in test instrument 113. As the probe package 300 is moved through an inside diameter of a test object under inspection, the receiver amplifier 110 detects a magnitude of any voltage difference between the first and second bridge terminals 107, 108 caused by defects in or on the test object.

In view of the foregoing, embodiments described herein provide an eddy current probe having a wide frequency range. It can operate at 400 Hz in carbon steel tubes with aluminum fins (i.e. tubes made from magnetic materials) and can be used with non-magnetic tubes such as brass, at 20 KHz test frequency, and stainless steel, at 300 KHz test frequency, as examples. A technical effect is to double the frequency range performance typical of common probes. Higher testing frequency provides cleaner signals and better data quality. It also provides an inspector a wider selection of lower frequencies to perform a back-up confirmation test of a test object undergoing inspection.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An eddy current probe for detecting a defect in a test object, the eddy current probe comprising:
   a first coil and a second coil both electrically connected to a first voltage terminal, the first voltage terminal being configured to receive a drive voltage, wherein the first coil and the second coil are drive coils; and
   a third coil and a fourth coil both electrically connected to a second voltage terminal, the second voltage terminal being configured to be coupled to a ground, wherein the third coil and the fourth coil are receive coils, and
   wherein the first coil is electrically connected to the third coil at a first bridge terminal, the second coil is electrically connected to the fourth coil at a second bridge terminal, the first coil is wound over the third coil, and wherein the first, second, third, and fourth coils are configured to indicate the defect in the test object by a voltage difference between the first and second bridge terminals when the four coils of the probe are inside the test object,
   wherein the first coil, second coil, third coil, and fourth coil are each located solely within the eddy current probe.

2. The eddy current probe of claim 1, further comprising at least one centering foot for centering the probe within an inside diameter of the test object as it travels through the test object.

3. The eddy current probe of claim 1, wherein an inductance of the first coil and the third coil are substantially equal.

4. The eddy current probe of claim 3, wherein an inductance of the second coil and the fourth coil are substantially equal.

5. The eddy current probe of claim 1, wherein the second coil is wound over the fourth coil.

6. A method of making an eddy current probe for inspecting a test object, the method comprising:
   winding a first, second, third, and fourth coil around a bobbin, wherein the steps of winding the first coil and winding the third coil comprise winding the first coil over the third coil;
   electrically connecting the first coil and the second coil to a first voltage terminal;
   electrically connecting the third coil and the fourth coil to a second voltage terminal;
   electrically connecting the first coil and the third coil to a first bridge terminal wherein the first coil and the second coil are drive coils; and
   electrically connecting the second coil and the fourth coil to a second bridge terminal, wherein the third coil and the fourth coil are receive coils,
   wherein the first coil, second coil, third coil, and fourth coil are each located solely within the eddy current probe.

7. The method of claim 6, further comprising electrically connecting a drive voltage to the first voltage terminal and electrically connecting a ground to the second voltage terminal.

8. The method of claim 7, further comprising electrically connecting an amplifier to the first and second bridge terminals.

9. The method of claim 6, further comprising disposing the first coil, the second coil, the third coil, the fourth coil, and the bobbin within a probe package, the probe package comprising a size for traveling through an inside diameter of the test object.

10. The method of claim 9, further comprising providing at least one centering foot on the probe package for centering the probe within the inside diameter of the test object as it moves through the test object.

11. The method of claim 6, wherein the steps of winding the second coil and winding the fourth coil comprise winding the second coil over the fourth coil.

12. A system for analyzing a defect in a test object, the system comprising:
   an eddy current probe, the probe comprising
      a first coil and a second coil both electrically connected to a first voltage terminal, the first voltage terminal being configured to receive a drive voltage, wherein the first coil and the second coil are drive coils,
      a third coil and a fourth coil both electrically connected to a second voltage terminal, the second voltage terminal being configured to bed coupled to a ground source, wherein the third coil and the fourth coil are receive coils, and
      wherein the first coil is electrically connected to the third coil at a first bridge terminal, the second coil is electrically connected to the fourth coil at a second bridge terminal, the first coil is wound over the third coil, wherein the first, second, third, and fourth coils are configured to indicate the defect in the test object by a voltage difference between the first and second bridge terminals; and
   a test instrument comprising:
      a drive voltage source electrically connected to the first terminal for providing the drive voltage,
      a ground source electrically connected to the second terminal for providing the ground, and
      a receiver amplifier electrically connected to the first and second bridge terminals for detecting a magnitude of the voltage difference,
   wherein the first coil, second coil, third coil, and fourth coil are each located solely within the eddy current probe.

13. The system of claim 12, wherein the probe further comprises at least one centering foot for centering the probe within an inside diameter of the test object as it travels through the test object.

14. The system of claim 12, wherein an inductance of the first coil and the third coil are substantially equal.

15. The system of claim 14, wherein an inductance of the second coil and the fourth coil are substantially equal.

16. The system of claim 12, wherein the second coil is wound over the fourth coil.

* * * * *